United States Patent
Cupp et al.

(10) Patent No.: US 6,841,178 B2
(45) Date of Patent: Jan. 11, 2005

(54) DENTAL CARE PET FOOD

(75) Inventors: Carolyn Jean Cupp, Liberty, MO (US); Lynn Ann Gerheart, Smithville, MO (US); Scott Schnell, St. Joseph, MO (US); Sheri Lynn Smithey, St. Joseph, MO (US); Donna Elizabeth Anderson, Weatherby Lake, MO (US)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/052,949

(22) Filed: Jan. 17, 2002

(65) Prior Publication Data

US 2002/0090444 A1 Jul. 11, 2002

Related U.S. Application Data

(63) Continuation of application No. 09/154,646, filed on Sep. 17, 1998.
(60) Provisional application No. 60/062,090, filed on Oct. 14, 1997.

(51) Int. Cl.⁷ ................................................ A01K 1/00
(52) U.S. Cl. ........................ 426/2; 426/623; 426/635; 426/805

(58) Field of Search ................................ 426/2, 53, 54, 426/805, 656, 658, 623, 635, 574; 424/49

(56) References Cited

U.S. PATENT DOCUMENTS

| 4,006,266 A | 2/1977 | Bone et al. |
| 4,364,925 A | 12/1982 | Fisher |
| 4,743,460 A | 5/1988 | Gellman et al. |
| 5,407,661 A | 4/1995 | Simone et al. |

FOREIGN PATENT DOCUMENTS

| EP | 0 645 095 A1 | 3/1995 |
| JP | 01 039953 | 2/1989 |

*Primary Examiner*—Keith Hendricks
(74) *Attorney, Agent, or Firm*—Bell, Boyd & Lloyd LLC

(57) ABSTRACT

A dried pet food which is able to mechanically clean the teeth of pets when chewed. The dried pet food is based on a matrix of a denatured protein source and a gelatinized carbohydrate source. Insoluble fiber is bound within the matrix. Further, a humectant is included within the gelatinized matrix is an amount sufficient for reducing the brittleness of the dried pet food.

9 Claims, No Drawings

DENTAL CARE PET FOOD

This application is a continuation of application Ser. No. 09/154,646, filed Sep. 17, 1998, which claims the benefit of Provisional application Ser. No. 60/062,090.

FIELD OF THE INVENTION

This invention relates to a dry pet food which reduces build up of dental plaque and calculus on the teeth of pets. The pet food, when chewed by pets, causes mechanical, abrasive cleaning of the pets' teeth.

BACKGROUND OF THE INVENTION

Many pets suffer from dental health problems. A primary factor in the development of these problems is the formation of plaque on the surface of the teeth. Plaque contains bacteria and other components that adhere to the surface of the teeth, accumulating both above and below the gum line and leading to inflammation, or gingivitis, and malodors in the dental cavity.

Contributing to the problem is the formation of tartar or dental calculus (mineralized plaque). Dental calculus forms on the tooth surface at or above the gum line and serves as a substrate for additional accumulation of plaque. Apart from causing gum irritation and eventually periodontal disease if left untreated, the calculus has an unsightly appearance.

Animals in the wild are less susceptible than pets to the formation of plaque and calculus due to the nature of the foods that they eat; many of these foods mechanically abrade plaque and calculus from the teeth. Pets, however, are usually fed commercially available pet foods. While the commercially available pet foods are usually much better for the pet from a nutritional point of view, they in general do not subject the teeth of the pets to abrasive forces sufficient to clean the teeth. Even dried kibbles are able to abrade the teeth only to a very limited extent. This is because dried kibbles usually crumble when chewed by the pet.

There have been various attempts to deal with the problem. One of these attempts centers around the use of chews made from rawhide or rawhide substitutes. By gnawing or chewing on the chews, the pet abrades calculus and plaque from its teeth. Further, as described in European patent application 0272968, various oral care agents may be incorporated into the chews. A drawback with this approach is that it is only really applicable to dogs. Cats are usually not in the habit of gnawing or chewing on a chew. Also, rawhide based products are expensive.

Another approach has been to incorporate oral care agents into certain pet foods. For example, U.S. Pat. No. 5,000,940 discloses baked dog biscuits which contain a tetrasodium pyrophosphate salt. The salt is reported in the patent to cause a reduction in calculus accumulation. Also, European patent application 0205354 discloses baked dog biscuits which contain vegetable fibers to abrade the teeth of the dog when chewed. The drawback with both these products is that the biscuit crumbles upon being bitten. Hence the dog does not chew the product and little abrasion occurs. This reduces the efficacy of the products. Also, the products are not really suitable for cats.

A further approach is described in U.S. Pat. No. 5,431,927. The pet food described in this patent is a dried product which contains aligned fibers and which, when chewed, fractures along striations rather then crumbles. This is reported in the patent to retain the product in contact with the animal's teeth for a longer period of time hence enhancing the abrasive effect. However, the product must be produced using a specially coated die which permits laminar flow conditions within the die. The laminar flow conditions are reported to cause alignment of the fibers within the product leading to the fracturing of the product when bitten. The use of these dies unnecessarily complicates production of the product.

Therefore there is a need for a dental care pet food which is applicable to both dogs and cats and which may be produced without the need for special processing.

SUMMARY OF THE INVENTION

Accordingly, in one aspect, this invention provides a dried pet food comprising a matrix including a denatured protein source, a gelatinized carbohydrate source; insoluble fiber; and a humectant in an amount sufficient for reducing brittleness of the matrix.

It is surprisingly found that the incorporation of a humectant and an insoluble fiber within a gelatinized matrix significantly reduces the brittleness of the pet food. Upon biting the pet food, the pet's teeth penetrate into the pet food for a longer distance prior to the pet food breaking. Hence the pet's teeth are in contact with the pet food for a longer time and are subjected to the abrasive effect of the pet food for a longer time.

Preferably the pet food contains about 0.5% to about 5% by weight of a humectant; for example about 1% by weight to about 3% by weight. The pet food preferably contains about 2% to about 15% by weight of insoluble fiber; for example about 3% to about 10% by weight.

The pet food preferably has a density of about 250 kg/m$^3$ to about 320 kg/m$^3$; for example about 270 kg/m$^3$ to about 300 kg/m$^3$. Further, the pet food preferably has a size such that the minimum distance from a center of gravity of the pet food to the surface of the pet food is about 3 mm; for example about 3.5 mm.

Preferably the pet food has a texture such that a probe, having a contact area of about 1 mm$^2$ and operated at a speed of about 5 mm/s, penetrates into the matrix for a distance of at least about 30% of the thickness of the matrix prior to breaking of the matrix; more preferably at least about 40%. For example, for a cat food, the probe may penetrate a distance of at least about 3 mm, preferably at least about 3.5 mm, prior to breaking of the matrix. For dog foods, the distance may be greater.

In a further aspect, this invention provides a method of reducing calculus and plaque build up on a pet's teeth, the method comprising administering to the pet a dried pet food having a gelatinized matrix including a protein source, a carbohydrate source, insoluble fiber, and a humectant, the pet food having reduced brittleness.

DETAILED DESCRIPTION OF PREFERRED EMBODIMENTS

Embodiments of the invention are now described, by way of example only.

The dried pet product is produced from a carbohydrate source, a protein source, insoluble fiber and a humectant. The dried pet food has reduced brittleness which maintains the pet food in contact with a pet's teeth for a longer period while being eaten. Hence the abrasive effect of the pet food on the teeth extends for a longer period.

The carbohydrate source is conveniently a grain such as corn, rice, wheat, beets, barley, oats, or soy, and mixtures of these grains. The grain is conveniently provided in the form of a flour or meal. Pure or substantially pure starches may also be used if desired. The exact carbohydrate source or sources used is not critical. In general the carbohydrate source is selected on the basis of cost and palatability considerations. It will be appreciated that the carbohydrate source may contain protein. The dried pet food conveniently contains about 20% to about 65% by weight of carbohydrate.

The protein source may be a vegetable protein source, an animal protein source, or a mixture of these protein sources. Suitable vegetable protein sources are gluten, wheat protein, soy protein, rice protein, corn protein, and the like. These proteins may be provided in the form of flours, concentrates and isolates as desired. Suitable animal protein sources are muscular or skeletal meat of mammals, poultry, and fish; meals such as meat meal, bone meal, fish meal, and poultry meal; by-products such as hearts, liver, kidneys, tongue and the like; and milk proteins. The dried pet food conveniently contains about 12% to about 50% by weight of protein; preferably more than about 25% by weight.

The insoluble fiber may be any suitable fiber. Examples of suitable fibers include soy fiber, rice hull fiber, pea hull fiber, oat hull fiber, barley hull fiber, sugar beet fiber, wheat bran fiber and pure cellulose. A suitable cellulose fiber is Solka-Floc®. The fiber is generally selected on the basis of cost and palatability considerations. However, a fiber which results in a lower density product is preferred; for example a cellulose fiber. The dried pet food conveniently contains about 2% to about 15% by weight of insoluble fiber.

The humectant may be any suitable humectant; for example glycerin, propylene glycol, butylene glycol, polyhydric glycols such as glycerol and sorbitol, and the like. The dried pet food conveniently contains about 0.5% to about 5% by weight of humectant.

If desired, abrasive agents may also be included. Suitable abrasive agents include ground oyster shells, titanium dioxide, and the like. Similarly dental care agents may also be included if desired; for example pyrophosphate salts such as tetrasodium pyrophosphate.

Various other ingredients, for example, salt, spices, seasonings, vitamins, minerals, flavoring agents, lipids and the like may also be incorporated into the dried pet product as desired. If added, the lipids may be any suitable animal fats; for example tallow, or may be vegetable fats.

The dried pet food may be produced in many different ways as desired. However extrusion gelatinization is found to be particularly suitable.

In a specific example of a suitable extrusion gelatinization process a dry feed mixture is prepared from a protein source, a carbohydrate source, insoluble fiber, vitamins and minerals. The dry feed mixture is then fed into a preconditioner.

In the preconditioner, water or steam, or both, is mixed into the dry feed mixture. Further, liquid flavor components, such as flavor digests or tallow, may be mixed into the dry feed mix in the preconditioner. Sufficient water, steam or liquid flavor components is mixed into the feed mixture to raise the moisture content of the dry feed mixture to about 10% to about 30% by weight. If desired, the temperature of the dry feed mixture may be raised in the preconditioner to about 60° C. to about 95° C. A suitable preconditioner is described in U.S. Pat. No. 4,752,139.

The moistened feed leaving the preconditioner is then fed into an extruder. The humectant is conveniently added to the moistened feed in the extruder. The extruder may be any suitable single or twin screw, cooking-extruder. Suitable extruders may be obtained from Wenger Manufacturing Inc, Clextral SA, Bühler AG, and the like. During passage through the extruder, the moistened feed passes through a cooking zone, in which it is subjected to mechanical shear and is heated to a maximum temperature of up to about 130° C., and a forming zone. The gauge pressure in the forming zone is about 600 kPa to about 10 MPa as desired. If desired, water or steam, or both, may be introduced into the cooking zone. Further, during passage through the extruder, the starch ingredients of the moistened feed are gelatinized to provide a gelatinized matrix of starch, protein, insoluble fiber and humectant.

The gelatinized matrix leaving the extruder is forced through a die. Any suitable die may be used. However the orifice of the die is preferably chosen such that the distance from the center of the orifice to any inner surface is at least about 3 mm. This ensures that the extrudate has a thickness of at least about 6 mm; more preferably at least about 8 mm. Further, the orifice is preferably substantially circular or substantially elliptical in cross-section. This provides an extrudate which is substantially circular or substantially elliptical in cross-section. This has the advantage that the end product does not have portions of reduced thickness which are easier for the animal to break when chewing.

Upon leaving the die, the extrudate is cut into pieces using blades. The blades are preferably arranged such that the pieces have a length of at least about 6 mm; for example about 8 mm. The individual pieces may then be processed as desired. For example they may be partially or fully dried and coated with further flavoring agents. After cooling, the pieces may be packed into suitable packages.

After drying, the pieces preferably have a moisture content of less than about 10% by weight; for example about 3% to about 7% by weight when leaving the drier. Further the pieces preferably have a density of about 250 kg/m$^3$ (about 15.6 lb/ft$^3$) to about 320 kg/m$^3$ (about 20 lb/ft$^3$); for example about 270 kg/m$^3$ (about 16.8 lb/ft$^3$) to about 300 kg/m$^3$ (about 18.7 lb/ft$^3$). The pieces preferably have a water activity of less than about 0.7; more preferably less than about 0.6.

Specific examples are now described for further illustration.

EXAMPLE 1

A dry mix is prepared from about 49% by weight of corn flour, about 19% by weight of corn gluten, about 8% by weight of fish and poultry meals, about 5% by weight of cellulose and various vitamins and minerals. The dry mix is fed into a preconditioner along with a flavor digest. The preconditioned mixture is then fed into an extruder along with about 2% by weight of glycerin. The preconditioner is operated at about 79° C. Steam is injected into the preconditioner at about 0.6 kg/minute and water at about 0.1 kg/minute.

The moistened feed leaving the preconditioner is then fed into a model 72 H extruder obtained from Clextral and gelatinized. The extruder has four zones and the temperatures in the four zones are about 69° C., about 88° C., about 125° C. and about 95° C. The pressure upon leaving the extruder is about 8.6 MPa gauge.

The gelatinized mixture is forced through the orifice of a die. The orifice is in the shape of an ellipse in cross section with a small diameter of 11 mm and a long diameter of 12 mm. The extrudate leaving the die is cut into pieces of 9 mm length. The pieces are then coated with flavoring agents and dried in the normal manner.

The pieces have a density of about 285 kg/m³ and a moisture content of about 6.5% by weight.

EXAMPLE 2

An amount of 100 dried pieces obtained using the process of example 1 are subjected to texture analysis using a TA-XT2 Texture Analyzer obtained from Stable Micro Systems, Inc. The Texture Analyzer is fitted with a rod-like probe which has a length of about 52 mm. The probe is made up of two sections; a first section and a second section. The first section has a length of about 21 mm and a constant diameter of about 9.5 mm. The second section tapers down to a point having a contact area of about 1 mm². The Texture Analyzer is operated at a speed of 5 mm/s and a contact force of 5 g. formation in each group. During the trial, the cats have ad libitum access to water and food and are fed once daily. The food consumption of each cat is monitored daily. The weight of each cat is recorded at the start of the trial and then upon weekly intervals.

On the day prior to the trial, each cat is subjected to complete dental prophylaxis in which all supra- and subgingival deposits of plaque and calculus are carefully removed. Also, the cat's teeth are thoroughly polished.

On the day of the trial, each group of cats is randomly allocated a different food product and fed. One group (Group 1) is fed the pieces of example 1, one group (Group A) is fed Purina Cat Chow; and one group (Group B) is fed Purina Meow Mix. After 7 days of being fed the same food products, a few drops of a 2 to 3% erythrosin plaque-disclosing solution are applied to the teeth of the cat and then thoroughly rinsed off with tap water. Plaque evaluation is then carried out on gingival and occlusal halves of the upper and lower canines, upper $3^{rd}$ and $4^{th}$ premolars, lower $3^{rd}$ and $4^{th}$ premolars, and lower $1^{st}$ molars. An assessment of the buccal tooth surface that is covered with plaque is made according to the following scale:

0=no observable plaque;

1=plaque covering less than 25% of the tooth surface;

2=plaque covering 25% to 50% of the tooth surface;

3=plaque covering 50% to 75% of the tooth surface; and

4=plaque covering greater than 75% of the tooth surface.

Plaque thickness is assessed as follows:

1=light or thin, a light pink color;

2=medium, a moderate or medium shade of red; and

3=heavy or thick, a dark bright shade of red.

A score is then obtained by multiplying the coverage score by the thickness score for each half of the 14 teeth to give a score ranging from 0 to 12. The score for each half of a tooth are added to provide a whole tooth score. The whole tooth scores are then averaged.

Each piece is placed on a base under the probe. The probe is moved downwardly and into the piece. The distance of penetration of the probe into the piece, the compression force and the time are recorded at a rate of 200 recordings per second. Breakage of the piece is determined upon a sharp fall off of the compression force. The distance of penetration, the compression force and the time are recorded at the moment of breakage. The values obtained for all pieces are then averaged.

For comparison, the process is repeated for each group of 100 pieces of commercially available products. The results are as follows:

| Product | Distance to breakage/mm |
| --- | --- |
| Example 1 | 3.58 |
| Hill's t/d | 3.54 |
| Hill's Maintenance | 1.87 |
| Friskies Ocean Fish | 1.20 |
| Purina Cat Chow | 1.05 |
| Purina Meow Mix | 1.05 |

The results indicate that the pieces of example 1 are at least equivalent to, in terms of resistance to breakage, the product believed to be produced according to the process described in U.S. Pat. No. 5,431,927. Both products are significantly better than standard dried pet foods.

Because the product of example 1 is resistant to breakage, the animal needs to bite deeper into each piece of the product before it breaks. Therefore the animal's teeth are subjected to improved mechanical cleaning.

EXAMPLE 3

A group of 45 healthy cats are used in the trial. Cats which are known to readily consume dried foods are selected. The cats are examined to identify those cats without obvious dental or oral cavity problems. The cats are then given a complete veterinary, physical examination. The cats are divided into three groups of 15 cats with an even distribution of cats susceptible to calculus On the $28^{th}$ day of the trial, evaluation of calculus is similarly performed for each animal on the proximal, mesial and distal thirds of the 14 teeth previous examined. The scores for each third of a tooth are added to provide a whole tooth score and all whole tooth scores are averaged.

Scores for all animals in each group are averaged and the results are as follows:

| Product | Plaque score at 7 days | Calculus score at 28 days |
| --- | --- | --- |
| Example 1 | 5.57 | 3.35 |
| Purina Cat Chow | 7.69 | 4.64 |
| Purina Meow Mix | 9.74 | 4.51 |

The results indicate that the product of example 1 shows significantly improved cleaning of the cats' teeth over commercially available dried foods. These results correlate with those of example 2.

EXAMPLE 4

The process described in example 1 is repeated except that a Wenger F165 single screw extruder is used in place of the Clextral extruder. The dried peices have substantially the same properties as those of example 1.

We claim:

1. A dried pet food comprising a gelatinized matrix comprising a protein source, a carbohydrate source, about 2% to about 15% by weight of insoluble fiber, about 0.5% to about 5% by weight of a humectant, and a moisture content ranging from about 3% to about 7% by weight.

2. A dried pet food according to claim 1 in which the humectant is glycerin.

3. A dried pet food according to claim 1 in which the insoluble fiber is a cellulose fiber.

4. A dried pet food according to claim 1 which has a density of about 250 kg/m$^3$ to about 320 kg/m$^3$.

5. A dried pet food according to claim 1 in the form of a cat kibble which has a length of at least 6 mm, a thickness of at least 6 mm, and in which the minimum distance from a center of gravity of the gelatinized matrix to a surface of the gelatinized matrix is about 3 mm.

6. A dried pet food comprising a matrix comprising a denatured protein source, a gelatinized carbohydrate source, about 2% to about 15% by weight insoluble fiber, a humectant; and the dried pet food having a moisture content ranging from about 3% to about 7% by weight.

7. A dried cat food kibble comprising a matrix comprising a gelatinized protein source, a gelatinized carbohydrate source, about 2% to about 15% by weight insoluble fiber, and a humectant, the kibble having a moisture content ranging from about 3% to about 7% by weight and a length of at least 6 mm, a thickness of at least 6 mm, and in which the minimum distance from a center of gravity of the matrix to a surface of the matrix is about 3 mm.

8. A method of reducing calculus and plaque build up on a pet's teeth, the method comprising administering to the pet a dried pet food comprising a gelatinized matrix including a protein source, a carbohydrate source, about 2% to about 15% by weight of insoluble fiber, and a humectant, the pet food having a moisture content ranging from about 3% to about 7% by weight.

9. A method of reducing calculus and plaque build up on a cat's teeth, the method comprising administering to the pet a dried kibble which contains a gelatinized matrix including a protein source, a carbohydrate source, about 2% to about 15% by weight of insoluble fiber and a humectant, a moisture content ranging from about 3% to about 7% by weight, and has a length of at least about 6 mm, a thickness of at least about 6 mm, and in which the minimum distance from a center of gravity of the matrix to a surface of the matrix is about 3 mm.

* * * * *